(12) United States Patent
Chantry et al.

(10) Patent No.: US 8,284,385 B2
(45) Date of Patent: Oct. 9, 2012

(54) WELDING ARC APPAREL WITH UV ACTIVATED IMAGES

(75) Inventors: Bruce John Chantry, Solon, OH (US);
Mark David McDowell, El Dorado Hills, CA (US)

(73) Assignee: Lincoln Global, Inc., City of Industry, CA (US)

( * ) Notice: Subject to any disclaimer, the term of this patent is extended or adjusted under 35 U.S.C. 154(b) by 320 days.

(21) Appl. No.: 12/618,231

(22) Filed: Nov. 13, 2009

(65) Prior Publication Data

US 2011/0116076 A1  May 19, 2011

(51) Int. Cl.
*G01N 21/00* (2006.01)
(52) U.S. Cl. ........................... 356/51; 250/474.1
(58) Field of Classification Search .............. 356/51; 250/474.1, 372; 2/8.8, 906; 116/201, 200
See application file for complete search history.

(56) References Cited

U.S. PATENT DOCUMENTS

| | | | |
|---|---|---|---|
| 3,597,054 A | 8/1971 | Winter | |
| 4,255,665 A | 3/1981 | Shriner | |
| 4,788,433 A | 11/1988 | Wright | |
| 4,882,598 A | 11/1989 | Wulf | |
| 5,500,532 A | 3/1996 | Kozicki | |
| 5,612,541 A | 3/1997 | Hoffmann et al. | |
| 5,731,589 A | 3/1998 | Sief et al. | |
| 5,986,273 A * | 11/1999 | Tripp et al. | 250/474.1 |
| 6,017,661 A | 1/2000 | Lindsay et al. | |
| 6,054,256 A | 4/2000 | Nohr et al. | |
| 6,060,223 A * | 5/2000 | Nohr et al. | 430/334 |
| 6,132,681 A * | 10/2000 | Faran et al. | 422/401 |
| 6,437,346 B1 | 8/2002 | Goudjil | |
| 6,818,904 B1 | 11/2004 | Ferren et al. | |
| 7,658,722 B2 | 2/2010 | Cude | |
| 7,709,812 B2 * | 5/2010 | Simon et al. | 250/474.1 |
| 2008/0185534 A1 | 8/2008 | Simon et al. | |
| 2008/0296513 A1 | 12/2008 | Ribi et al. | |
| 2009/0194708 A1 | 8/2009 | Studer et al. | |
| 2009/0224168 A1 | 9/2009 | Santibanez-Viani et al. | |

FOREIGN PATENT DOCUMENTS

| | | |
|---|---|---|
| CN | 201323898 Y | 10/2009 |
| EP | 1 123 814 A2 | 8/2001 |
| EP | 1637046 A2 | 3/2006 |
| WO | 96/39302 A2 | 12/1996 |
| WO | 2008037076 A1 | 4/2008 |

OTHER PUBLICATIONS

International Search Report for application PCT/IB2010/02908, May 2012.
Written Opinion for application PCT/IB2010/02908, 2011.

* cited by examiner

*Primary Examiner* — Layla Lauchman
(74) *Attorney, Agent, or Firm* — Hahn Loeser & Parks LLP

(57) ABSTRACT

A welding accessory and a system for detecting UV radiation exposure during welding operations are disclosed. The welding accessory may have a surface exposed to UV radiation generated by electric arc welding, a first image visible without exposure to the UV radiation, and a second image formed from UV activated dye that is visible only after exposure to UV radiation generated by the electric welding arc. A system may include a UV exposure indicator with a first state and at least a second state, and include UV activated dye adapted to provide a reversible or persistent visual indication upon exposure to UV radiation. The visual indication may include any combination of symbols, logos, images, text, or other decorative or informational designs as desired.

19 Claims, 7 Drawing Sheets

WELDING ARC APPAREL WITH UV ACTIVATED IMAGES

TECHNICAL FIELD

The present disclosure relates to welding accessories, and more specifically, to welding apparel with images activated by UV radiation from an electric welding arc.

BACKGROUND

Welding is an important process in the manufacture and construction of various products and structures. Applications for welding are widespread and used throughout the world including, for example, the construction and repair of ships, buildings, bridges, vehicles, and pipe lines, to name a few. Welding is performed in a variety of locations, such as in a factory with a fixed welding operation or on site with a portable welder.

In manual or semi-automated welding a user/operator (i.e. welder) directs welding equipment to make a weld. For example, in electric arc welding the welder may manually position a welding rod or welding wire and produce a heat generating arc at a weld location. In this type of welding, the spacing of the electrode from the weld location is related to the arc produced and to the achievement of optimum melting/ fusing of the base and welding rod or wire metals. The quality of such a weld is often directly dependant upon the skill of the welder.

The electric welding arc is known to produce ultraviolet (UV) radiation. The UV radiation produced by the electric welding arc is capable of causing injury comparable to a sun burn. The UV radiation has also been known to cause eye irritation, a condition commonly referred to as "welder's flash" or "arc eye." The intensity of the UV radiation produced during electric arc welding depends upon many factors such as the process type, welding parameters, electrode and base metal composition, fluxes, and any coating or plating on the base metal. Additionally, tip size, shielding gas, and filler metal composition are among other variables that affect the amount of UV radiation generated. In addition to direct exposure to UV radiation, UV radiation can reflect from surfaces common in a welding environment, such as unpainted metals and concrete floors, resulting in indirect exposure. Further, the effects of UV radiation exposure are cumulative and repeated exposure can result in retinal injury and other health hazards.

UV radiation is commonly divided into three bands, UV-A, UV-B, and UV-C, in order of decreasing wavelength. Natural sunlight is the most prevalent source of UV radiation in all three bands, however UV-C is substantially absorbed by the ozone layer. Generally UV-A has a wavelength from 320 to 380 nanometers; UV-B has a wavelength from 290 to 320 nanometers; and UV-C has a wavelength from 200 to 290 nanometers. The shorter the wavelength the greater the biological effects of the UV radiation. Electric arc welding produces UV radiation in all three bands, but has substantial emissions in the upper end of the UV-C band.

In the past, various methods and devices have been used to shield welders from the UV radiation produced by electric arcs. For example, welding helmets, jackets, and gloves are customarily worn that substantially block UV radiation from reaching the welder's eyes and body. In the welding environment, other personnel also commonly wear personal protective equipment such as safety glasses that limit exposure to UV radiation.

The extent of UV exposure for personnel working around welding arcs varies greatly and is often not precisely known. To limit unintended exposure to nearby persons, curtains and shields of various types have been constructed to isolate the welding operation. The reflection of UV radiation from unpainted metal, concrete, and other surfaces however limits the effectiveness of shielding the welding operation. Welding operations have also been located away from walkways, aisles, and other areas where other personnel are working to reduce exposure to the other personnel, however, this is often impractical when welding operations are conducted in confined areas. Other techniques for avoiding UV exposure have also been employed including placing warning signs around the welding environment highlighting the potential for UV exposure.

SUMMARY

This present disclosure relates to welding accessories that are capable of providing a visual indication of the presence of UV radiation generated by an electric welding arc during a welding operation. The welding accessories may, for example, include welding helmets, welding jackets, welding shirts, hard hats, cloth skull caps, ball cap style hats, safety glasses, gloves, badges, work boots, belts, and jewelry, in addition to other accessories used in a welding environment. The visual indication may be a transition between a first image and a second image, and the transition may be permanent or reversible. The welding accessory may be a welding helmet, welding jacket, gloves, safety glasses, indicator badge, or other welding accessory. One or more UV activated dyes, pigments or inks may be employed to provide the indication in the presence of UV radiation from the electric welding arc. It must be understood, as used in this application the term "UV activated dye" is to include UV activated dyes, pigments, inks and any other similar substance. A UV exposure indicator may also have a first state and at least a second state, where the visual indication is a transition between the first state and at least the second state. Various symbols, logos, text, images, or other decorative or informational designs may be employed to indicate the presence or absence of UV radiation.

Also disclosed is a system for detecting cumulative UV radiation exposure during welding operations having a UV exposure indicator with graduated states. UV radiation exposure may also be detected by providing a welding system and a UV exposure indicator, and operating the welding system to generate UV radiation while monitoring the UV exposure indicator and ceasing welding operations after a predetermined level of UV exposure is indicated.

Various aspects of the present disclosure will become apparent to those skilled in the art from the following detailed description and the accompanying drawings.

DETAILED DESCRIPTION

Figure 1:
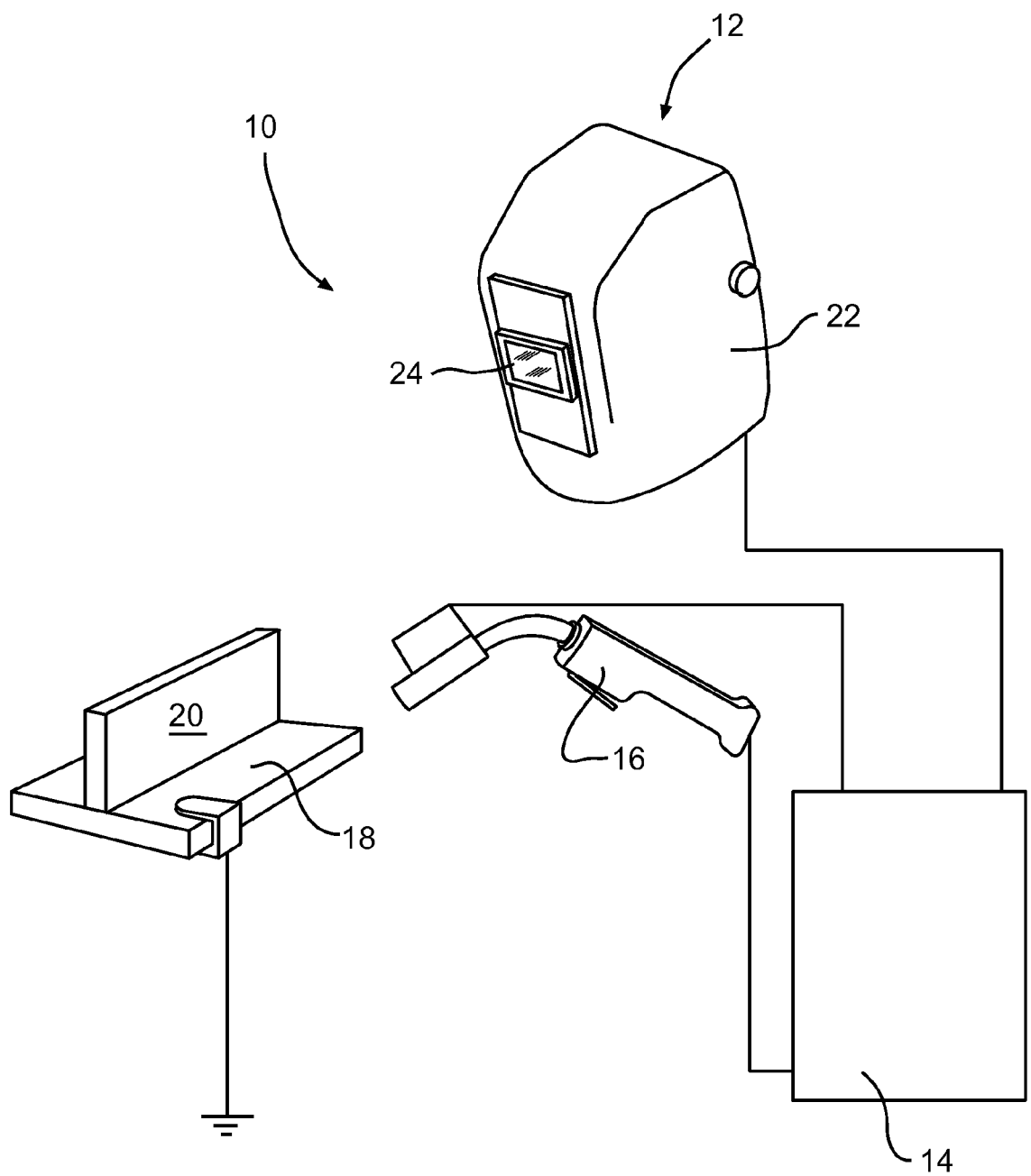
FIG. 1 is a schematic view of a welding environment.

Referring now to the drawings, FIG. 1 illustrates a welding environment 10. The welding environment 10 may include a welding helmet 12, a welding system 14, a welding gun 16, and a work piece 18. The welding environment may also, for example, include a stick electrode holder, TIG torch or other apparatus for use with electric arc welding. The work piece 18 generally defines a welding work area 20 where the welding gun may be used to form a weld. Various types of exemplary welding, including Shielded Metal Arc Welding (SMAW), Gas Metal Arc Welding (GMAW) e.g. MIG melding, and Gas Tungsten Arc Welding (GTAW) e.g. TIG welding, may be conducted in the welding environment.

The welding system 14 includes welding equipment for generating a welding current and voltage, a welding control system for controlling the welding current and voltage, and a monitoring system for monitoring the welding current and voltage. The monitoring system may also monitor a variety of other operating parameters, such as but not limited to, welding wire feed speed, amount of welding wire remaining, any type of welding feedback desired by the operator, and any other desired operating parameters.

Referring generally to FIGS. 1-7, presently disclosed is a welding accessory comprising a surface exposed to an electric welding arc during a welding operation, the surface having a first image and a second image, the first image being visible on the surface of the welding accessory without exposure to the electric welding arc, and the second image formed from UV activated dye on the surface and visible only after exposure to UV radiation generated by the electric welding arc during the welding operation. The welding accessory may be welding helmets, welding jackets, welding shirts, safety glasses, gloves, badges, work boots, belts, or jewelry, or any other suitable accessories used or worn in a welding environment that may have a surface exposed to UV radiation.

During operation, the welding system 14 operates to generate an electric welding arc between welding gun 16 and work piece 18. In other examples, the welding system 14 may generate an electric welding arc between a stick electrode holder, a GTAW or TIG torch or another welding apparatus and the work piece 18. In each example, the electric welding arc generates electromagnetic radiation including emissions in the UV, visible light, and infrared spectra. The UV radiation generated by the electric welding arc may include radiation in the UV-A, UV-B, and UV-C bands. Frequently, the UV radiation produced by electric welding arcs may be concentrated in the UV-C band between approximately 200 and 290 nanometers in wavelength. The UV radiation may be further concentrated between approximately 260 and 280 nanometers in wavelength.

A welding accessory may have a first image visible on the surface of the welding accessory without exposure to the electric welding arc. For example, the first image may be a logo, symbol, text, or other decorative or informational design. Alternatively, the first image may be the undecorated surface of the welding accessory. For example, the outer surface 22 of the welding helmet 12 may have a first image such as a company logo.

A welding accessory may also have a second image formed from UV activated dye on the surface of the welding accessory, where the second image is visible only after exposure to UV radiation generated by the electric welding arc during the welding operation. The second image may also be a logo, symbol, text, or other decorative or informational design as desired. For example, the second image may be a warning symbol indicating the presence of UV radiation or may be a warning indicative of exposure to at least a predetermined amount of UV radiation. In another example, the second image may be a decorative design identifying the provider of the welding accessory.

Figure 2:
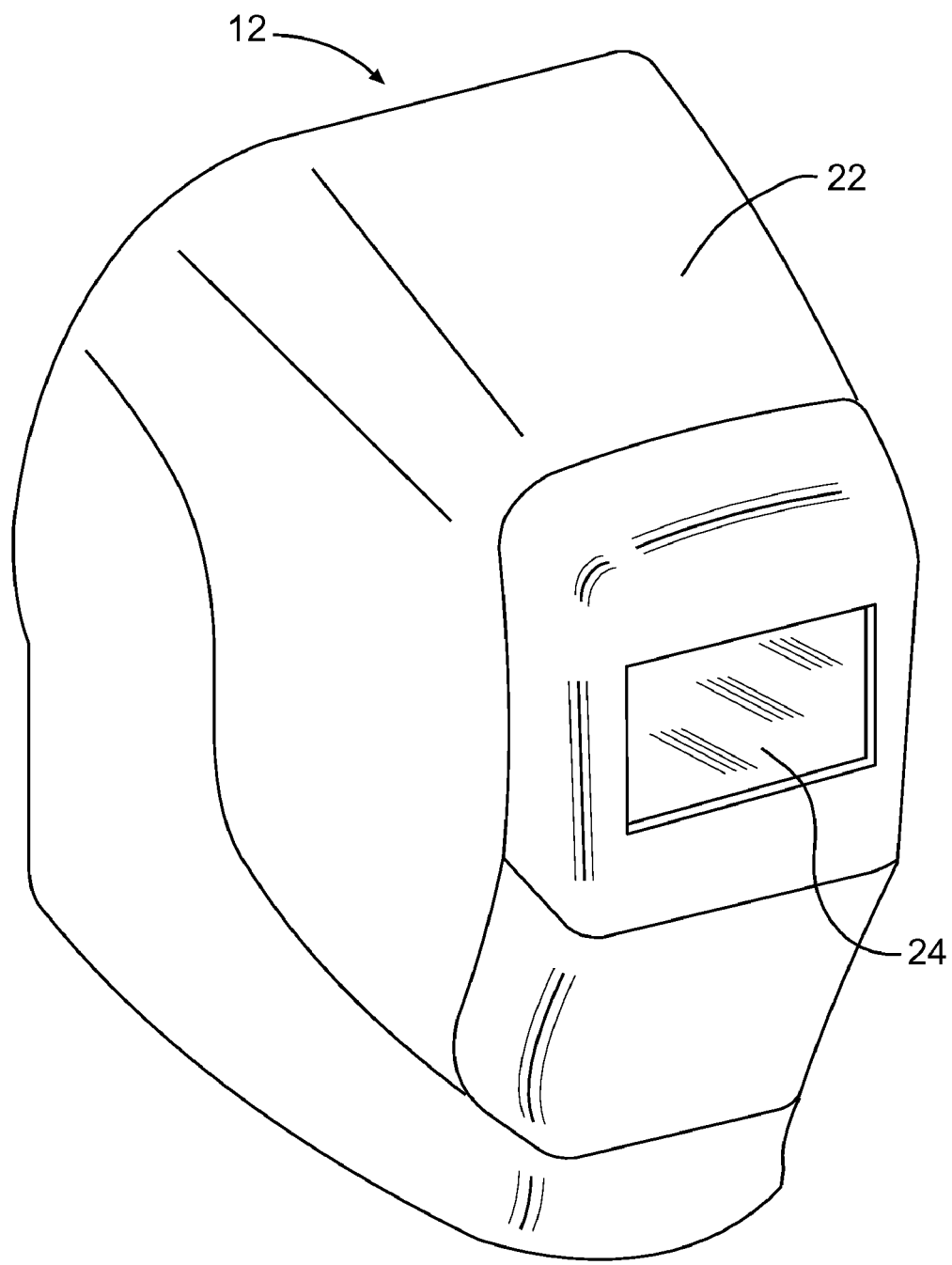
FIG. 2 is a perspective view of a welding helmet.
Figure 3:
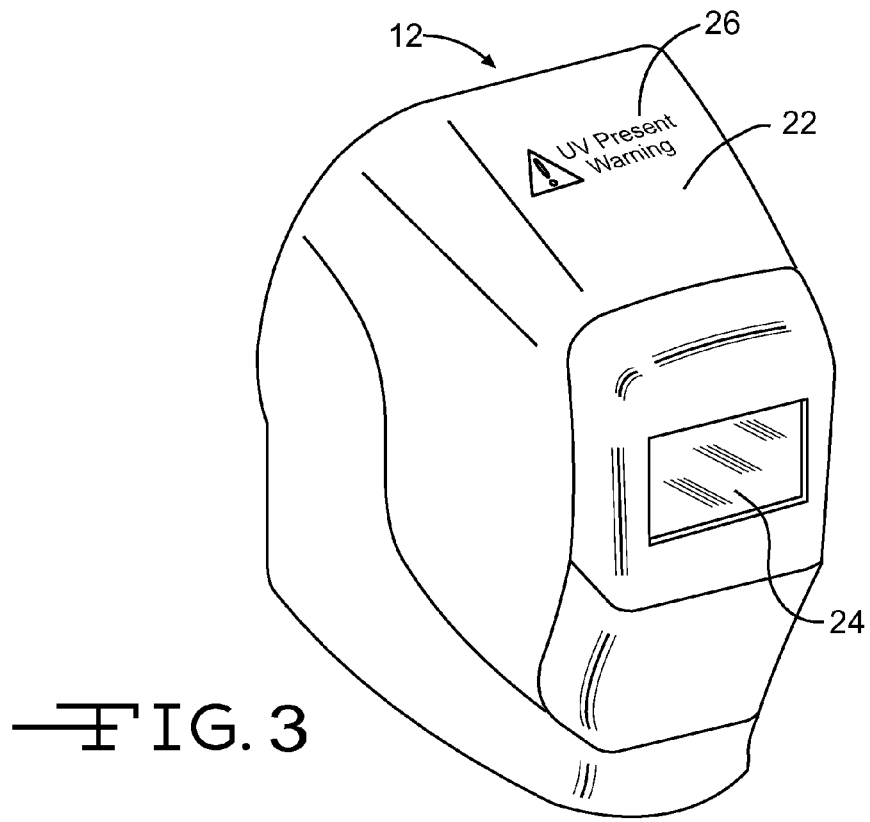
FIG. 3 is a perspective view of a welding helmet after exposure to UV radiation.
Figure 4:
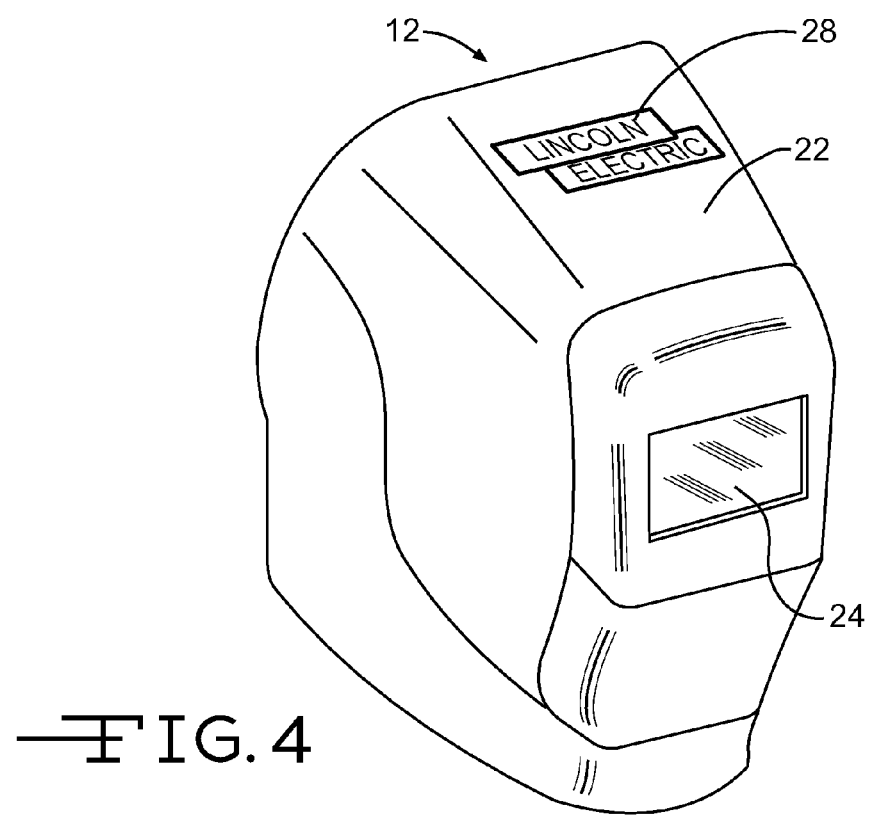
FIG. 4 is a perspective view of another welding helmet after exposure to UV radiation.

Referring to FIGS. 2 through 4, a welding helmet 12 having an outer surface 22 and a view port 24 is illustrated. The welding helmet 12 may shield the welder's head and eyes from the electric welding arc and the UV radiation generated by the electric welding arc. The welding helmet 12 may also protect the welder from heat, sparks, and other hazards commonly encountered in a welding environment. The outer surface 22 of the welding helmet 12 is exposed to the electric welding arc during the welding operation.

As shown in FIG. 2, the outer surface 22 has a first image which is the undecorated surface of the welding helmet. The outer surface 22 also has a second image formed from UV activated dye. The second image may be a warning symbol 26 such as that illustrated in FIG. 3. The second image may be a company logo 28 such as that illustrated in FIG. 4. As will be apparent, the second image may be selected from numerous designs as desired.

The second image is formed from a UV activated dye on the surface of the welding accessory. The UV activated dye forming the second image may be integrated into the material forming the surface of the welding accessory. Alternatively, the UV activated dye may be applied to the surface of the welding accessory. In yet another alternative, the UV activated dye may be incorporated into a UV exposure indicator, and attached to the surface of the welding accessory in the form of a badge, sticker, or other comparable device.

A UV activated dye or pigment may generally be described as a substance that undergoes a change of color or state upon exposure to UV radiation. UV activated dyes have also been referred to as photochromatic, photochangeable, and photoreactive dyes. As used herein, the term UV activated dye is intended to represent substances that undergo a change of color or state upon exposure to UV radiation. Various UV activated dyes are known and commercially available, and are contemplated for use with the present disclosure. UV activates dyes that respond to UV radiation but are stable in the presence of natural sunlight or artificial lights are known such as those disclosed in U.S. Pat. No. 6,054,256 to Nohr et al. or U.S. Patent Application 2008/0296513 to Ribi et al. The UV activated dyes may be selected to respond to specific wavelengths of UV radiation. For example, a UV activated dye may be selected to respond to wavelengths between 200 and 290 nanometers. In another example, a UV activated dye may be selected to respond to wavelengths between 260 and 280 nanometers. A combination of UV activated dyes and non-activated materials may be utilized to provide the desired characteristics. These and other known UV activated dyes may be employed with the present disclosure.

As described in U.S. Pat. No. 6,054,256 to Nohr et al, one UV activated dye, an irreversible ultraviolet radiation transorber that is erasable/mutable, is exemplified by an ultraviolet radiation transorber/mutable colorant/molecular includant complex where the mutable colorant is malachite green or Victoria Pure Blue BO (Basic Blue 7) and, the ultraviolet radiation transorber is IRGACURE 184 (1-hydroxycyclohexyl phenyl ketone), and the molecular includant is β-cyclodextrin.

In further examples, as described in U.S. Pat. No. 6,054,256 to Nohr et al, an exemplary and non-limiting list of mutable colorants includes triarylmethyl dyes, such as Malachite Green Carbinol base {4-(dimethylamino)-α-[4-(dimethylamino)phenyl]-α-phenylbenzene-methanol}, Malachite Green Carbinol hydrochloride {N-[[4-(dimethylamino)

phenyl]phenylmethylene]-2,5-cyclohexyldien-1-ylidene]-N-methyl-methanaminium chloride or bis[p-(dimethylamino)phenyl]phenylmethylium chloride}, and Malachite Green oxalate {N-4-[[4-(dimethylamino)phenyl] phenylmethylene]-2,5-cyclohexyldien-1-ylidene]-N-methylmethanaminium chloride or bis[p-dimethylamino)phenyl] phenylmethylium oxalate}; monoazo dyes, such as Cyanine Black, Chrysoidine [Basic Orange 2; 4-(phenylazo)-1,3-benzenediamine monohydrochloride], Victoria Pure Blue BO, Victoria Pure Blue B, basic fuschin and β-Naphthol Orange; thiazine dyes, such as Methylene Green, zinc chloride double salt [3,7-bis(dimethylamino)-6-nitrophenothiazin-5-ium chloride, zinc chloride double salt]; oxazine dyes, such as Lumichrome (7,8-dimethylalloxazine); naphthalimide dyes, such as Lucifer Yellow CH {6-amino-2-[(hydrazinocarbonyl) amino]-2,3-dihydro-1,3-dioxo-1H-benz[de]isoquinoline-5, 8-disulfonic acid dilithium salt}; azine dyes, such as Janus Green B {3-(diethylamino)-7-[[4-(dimethylamino)phenyl] azo]-5-phenylphenazinium chloride}; cyanine dyes, such as Indocyanine Green {Cardio-Green or Fox Green; 2-[7-[1,3-dihydro-1,1-dimethyl-3-(4-sulfobutyl)-2H-benz[e]indol-2-ylidene]-1,3,5-heptatrienyl]-1,1-dimethyl-3-(4-sulfobutyl)-1H-benz[e]indolium hydroxide inner salt sodium salt}; indigo dyes, such as Indigo {Indigo Blue or Vat Blue 1; 2-(1,3-dihydro-3-oxo-2H-indol-2-ylidene)-1,2-dihydro-3H-indol-3-one}; coumarin dyes, such as 7-hydroxy-4-methyl-coumarin (4-methylumbelliferone); benzimidazole dyes, such as Hoechst 33258 [bisbenzimide or 2-(4-hydroxyphenyl)-5-(4-methyl-1-piperazinyl)-2,5-bi-1H-benzimidazole trihydrochloride pentahydrate]; paraquinoidal dyes, such as Hematoxylin {Natural Black 1; 7,11b-dihydrobenz[b]indeno [1,2-d]pyran-3,4,6a,9,10(6H)-pentol}; fluorescein dyes, such as Fluoresceinamine (5-aminofluorescein); diazonium salt dyes, such as Diazo Red RC (Azoic Diazo No. 10 or Fast Red RC salt; 2-methoxy-5-chlorobenzenediazonium chloride, zinc chloride double salt); azoic diazo dyes, such as Fast Blue BB salt (Azoic Diazo No. 20; 4-benzoylamino-2,5-diethoxybenzene diazonium chloride, zinc chloride double salt); phenylenediamine dyes, such as Disperse Yellow 9 [N-(2,4-dinitrophenyl)-1,4-phenylenediamine or Solvent Orange 53]; diazo dyes, such as Disperse Orange 13 [Solvent Orange 52; 1-phenylazo-4-(4-hydroxyphenylazo)naphthalene]; anthraquinone dyes, such as Disperse Blue 3 [Celliton Fast Blue FFR; 1-methylamino-4-(2-hydroxyethylamino)-9, 10-anthraquinone], Disperse Blue 14 [Celliton Fast Blue B; 1,4-bis(methylamino)-9,10-anthraquinone], and Alizarin Blue Black B (Mordant Black 13); trisazo dyes, such as Direct Blue 71 {Benzo Light Blue FFL or Sirius Light Blue BRR; 3-[(4-[(4-[(6-amino-l-hydroxy-3-sulfo-2-naphthalenyl)azo]-6-sulfo-1-naphth alenyl)azo]-1-naphthalenyl)azo]-1,5-naphthalenedisulfonic acid tetrasodium salt}; xanthene dyes, such as 2,7-dichlorofluorescein; proflavine dyes, such as 3,6-diaminoacridine hemisulfate (Proflavine); sulfonaphthalein dyes, such as Cresol Red (o-cresolsulfonaphthalein); phthalocyanine dyes, such as Copper Phthalocyanine {Pigment Blue 15; (SP-4-1)-[29H,31H-phthalocyanato(2-)-$N^{29}$, $N^{30}$,$N^{31}$,$N^{32}$]copper}; carotenoid dyes, such as trans-.beta.-carotene (Food Orange 5); carminic acid dyes, such as Carmine, the aluminum or calcium-aluminum lake of carminic acid (7-a-D-glucopyranosyl-9,10-dihydro-3,5,6,8-tetrahydroxy-1-methyl-9,10-dioxo-2-anthracenecarbonylic acid); azure dyes, such as Azure A [3-amino-7-(dimethylamino)phenothiazin-5-ium chloride or 7-(dimethylamino)-3-imino-3H-phenothiazine hydrochloride]; and acridine dyes, such as Acridine Orange [Basic Orange 14; 3,8-bis (dimethylamino)acridine hydrochloride, zinc chloride double salt] and Acriflavine (Acriflavine neutral; 3,6-diamino-10-methylacridinium chloride mixture with 3,6-acridinediamine).

As further described in U.S. Pat. No. 6,054,256 to Nohr et al., a non-limiting and exemplary list of the irreversible ultraviolet radiation transorber may include a stabilizing compound, such as, phthaloylglycine-2959, DARCUR 2959, and other photoreactors such as 1-hydroxy-cyclohexyl-phenyl ketone ("HCPK") (IRGACURE 184, Ciba-Geigy); α,α-dimethoxy-α-hydroxy acetophenone (DAROCUR 1173, Merck); 1-(4-isopropylphenyl)-2-hydroxy-2-methyl-propan-1-one (DAROCUR 1116, Merck); 1-[4-(2-hydroxyethoxy)phenyl]-2-hydroxy-2-methyl-propan-1-one (DAROCUR 2959, Merck); poly[2-hydroxy-2-methyl-1-[4-(1-methylvinyl)phenyl]propan-1-one] (ESACURE KIP, Fratelli Lamberti); benzoin (2-hydroxy-1,2-diphenylethanone) (ESACURE BO, Fratelli Lamberti); benzoin ethyl ether (2-ethoxy-1,2-diphenylethanone) (DAITOCURE EE, Siber Hegner); benzoin isopropyl ether (2-isopropoxy-1,2-diphenylethanone) (VICURE 30, Stauffer); benzoin n-butyl ether (2-butoxy-1,2-diphenylethanone) (ESACURE EB1, Fratelli Lamberti); mixture of benzoin butyl ethers (TRIGONAL 14, Akzo); benzoin iso-butyl ether (2-isobutoxy-1,2-diphenylethanone) (VICURE 10, Stauffer); blend of benzoin n-butyl ether and benzoin isobutyl ether (ESACURE EB3, ESACURE EB4, Fratelli Lamberti); benzildimethyl ketal (2,2-dimethoxy-1,2-diphenylethanone) ("BDK") (IRGACURE 651, Ciba-Geigy); 2,2-diethoxy-1,2-diphenylethanone (UVATONE 8302, Upjohn); α,α-diethoxyacetophenone (2,2-Diethoxy-1-phenyl-ethanone) ("DEAP", Upjohn), (DEAP, Rahn); and α,α-di-(n-butoxy)-acetophenone (2,2-dibutoxyl-1-phenylethanone) (UVATONE 8301, Upjohn)

U.S. Patent Application 2008/0296513 to Ribi et al. describes several examples of photochromic agents including diynes (conjugated diacetylenes), and in particular acid, ester, urethane, amide, nitrile, or alcohol monomers of at least about 8 carbon atoms, and not more than about 36 carbon atoms, more usually from about 12 to 30 carbon atoms. These acetylenic groups may generally be displaced from the terminal carbon atoms by at least 1 carbon atom. Various derivatives of the functional groups of the diynes can serve to modify the properties of the diynes for use in a particular formulation. As described in U.S. Patent Application 2008/0296513 to Ribi et al, a transparent UV activated paint/polish may be made by adding the monomer 10,12-pentacosadiyneoic, acid (PDA) to a clear commercially available nail polish finish (such as Orly Snap, Orly International, Inc., made with ethyl acetate, butyl acetate, isopropyl alcohol, nitrocellulose, dibutylphthalate, polyvinyl butyral, etocrylene, D&C red #6 barium lake, D&C violet #2) or to a commercially available clear coat paint to a final concentration of 100 PDA/ml polish/paint finish. The PDA monomer was mixed to clarity. Thin films may then be applied to surfaces to be exposed to UV radiation. Also described in U.S. Patent Application 2008/0296513 to Ribi et al., stick-on sensor tabs may include transparent tape stickers (e.g. ¼ inch in diameter circles made with acrylic based adhesive label dye cut and placed on a convenient removal strip) coated with a solution of 100 mg PDA/ml chloroform with a coating thickness of about 200 microns.

For example, one non-limiting example of a suitable photochrome for UV dye is a spirooxazine. The spiro form of an oxazine is a colorless leuco dye; the conjugated system of the oxazine and another aromatic part of the molecule is separated by a spa-hybridized "spiro" carbon. After irradiation with UV light, the bond between the spiro-carbon and the oxazine breaks, the ring opens, the spiro carbon achieves $sp^2$ hybridization and becomes planar, the aromatic group rotates, aligns its π-orbitals with the rest of the molecule, and a conjugated system forms with ability to absorb photons of visible light, and therefore appear colorful. When the UV source is removed, the molecules gradually relax to their ground state, the carbon-oxygen bond reforms, the spiro-carbon becomes spa hybridized again, and the molecule returns to its colorless state. This example illustrates a reversible color-change.

In another non-limiting example, a suitable UV is a UV sensitive composition that undergoes a color change upon exposure to a predetermined dosage of UV-C radiation, such as disclosed in U.S. Pat. No. 7,598,331 to Havens, et al. The UV-C sensitive composition includes a halogenated polymer, such as polyvinylidene chloride, that produces an acid upon exposure to UV radiation, and a pH sensitive dye. Upon exposure to UV-C radiation, the halogenated polymer undergoes degradation and produces HCl. The pH sensitive dye changes color as a result in an increase in HCl in the system. This composition may also include an acid scavenging composition and/or a diluent to control the amount of HCl produced in the system. The amount of HCl liberated from UV-C exposure may be selectively controlled so that a color change may be produced at a desired UV-C dosage. This example illustrates a unidirectional color change.

As described in U.S. Pat. No. 7,598,331 to Havens, et al, the halogenated polymer may be polyvinyl chloride (PVC), polyvinylidene chloride (PVDC), ethylene-chlorotrifluoroethylene copolymer, chlorinated rubber, and copolymers thereof and in some cases the halogenated copolymers may also be combined with one or more monomers that have little or no halogen content. The pH sensitive dye may be bromophenol blue, phenol red, thymol blue, ethyl orange, m-Cresol purple, New Fuchsin, p-methyl red, lissamine green, aniline blue, methyl violet, crystal violet, ethyl violet, brilliant green, oralochite green oxalate, methyl green, cresol red, quinaldine red, para methyl red, bromothymol blue, metanil yellow, orange IV, phenylazoaniline, erythrosin B, benzopurpurin 4B, congo red, methyl orange, resazurin, methyl red, alizarin red, bromocresol purple, chlorophenol red, or combinations of dyes for multiple color changes.

In a further non-limiting example, the UV dye may be a "diarylethen." Diarylethens generally have a high thermodynamic stability. Diarylethens operate by means of a 6-π electrocyclic reaction, the thermal analog of which is impossible due to steric hindrance. Some other photochromic dyes have the appearance of a crystalline powder, and in order to achieve the color change, they may have to be dissolved in a solvent or dispersed in a suitable matrix. However, some diarylethenes require so little shape change upon isomerization that they have the advantage that they may be converted between states while remaining in crystalline form.

Additionally, the UV dye may be Spectrachrome® crystals, U.S. trademark Reg. No. 2,531,301 registered to Del Sol, L.C. In this example, among others, the dye may be employed into thread to be embroidered on to an article.

During a welding operation, the electric welding arc generates UV radiation that reaches a surface of the welding accessory. The UV activated dye forming the second image on the surface of the welding accessory responds to the UV radiation causing the second image to appear indicating the present of UV radiation. The appearance or presence of the second image on the welding accessory may alert the welder and other persons near the welding operation that UV radiation is present and that appropriate precautions should be employed. The first image and second image may be selected to highlight the presence of UV radiation or may be selected for other reasons.

Figure 5A:
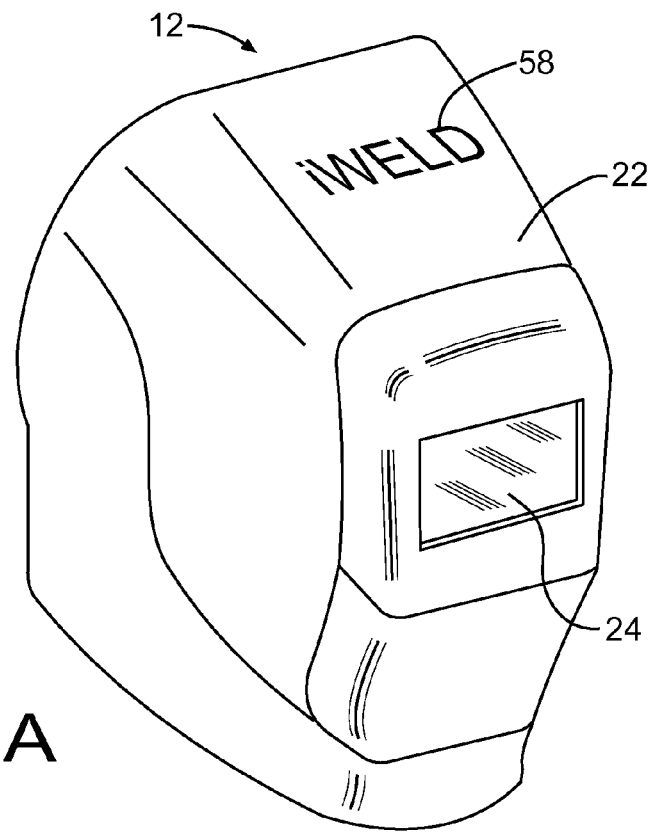
FIGS. 5A-B are perspective views of yet another welding helmet.
Figure 5B:
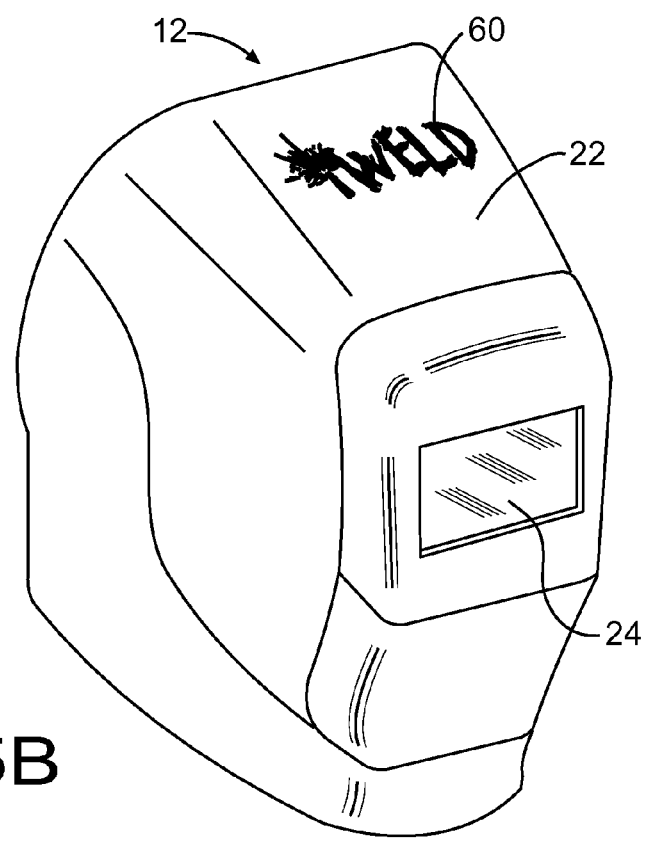

Other embodiments include a variety of other welding accessories. For example, referring generally to FIGS. 5A and 5B, another welding helmet 12 is illustrated. The welding helmet 12 has a primary image 58 visible without exposure to the electric welding arc as shown in FIG. 5A. The welding helmet 12 also has a secondary image 60 formed from UV activated dye as shown in FIG. 5B. As FIGS. 5A and 5B illustrate, the first image and the second image may overlap. Also, the first image and the second image may combine to form a composite image on the surface of the welding accessory. This combination of the first image and the second image permits integration of various logos, symbols, text, and other decorative or informational designs when applied to the welding accessories.

Figure 6A:
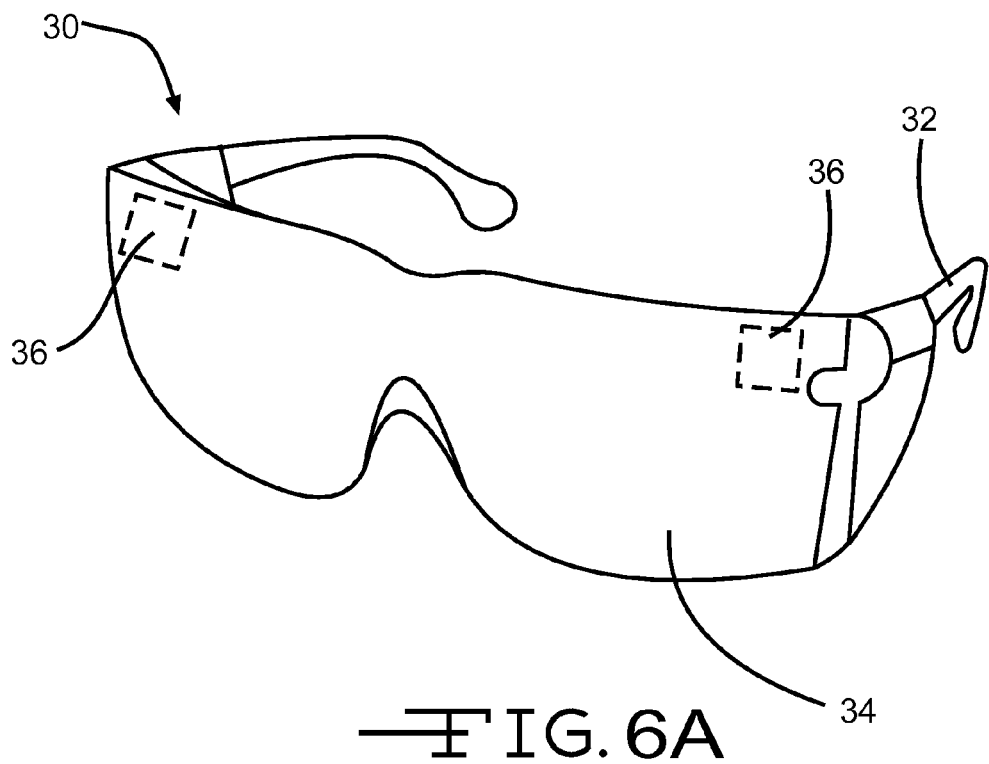
FIGS. 6A-B are perspective views of safety glasses.
Figure 6B:
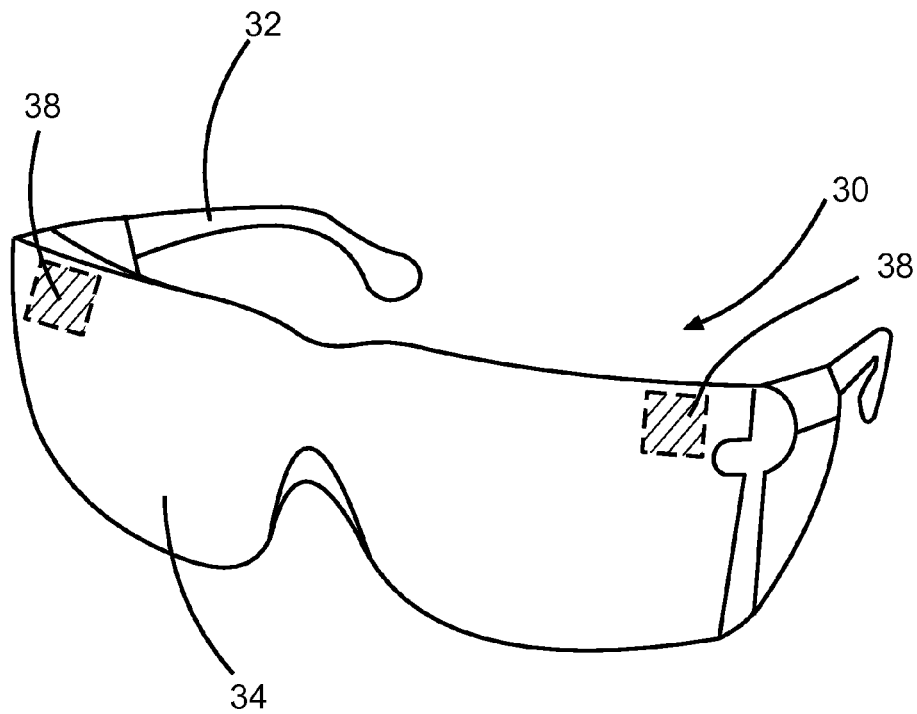

Referring generally to FIGS. 6A and 6B, safety glasses 30 are illustrated having a frame 32 and lens 34. Safety glasses 30 such as those illustrated are commonly required in and around building, construction, and repair sites where welding operations occur. The safety glasses may also have one or more UV exposure indicators 36. As shown in FIG. 6A, a UV exposure indicator 36 may be positioned on the lens 34. Alternatively the UV exposure indicator may be positioned on the frame 32. In one embodiment, the entire frame 32 may be a UV exposure indicator. Upon exposure to UV radiation, the UV exposure indicator 36 may change color or otherwise visually indicate the presence of UV radiation. As shown in FIG. 6B, the indicator transitions to a darkened indicator 38. The UV exposure indicator may be formed from or include UV activated dyes as previously discussed. In one embodiment the indicator may be positioned on the outside of the lens 34. In another embodiment the indicator may be positioned on the inside of the lens 34. Positioning the indicator on the inside of the lens may provide a better indication of UV radiation reaching the eye. Both a person wearing the safety glasses 30 as well as other persons in and around the welding environment 10 may be alerted to the presence of UV radiation by the UV exposure indicator 36.

Figure 7A:
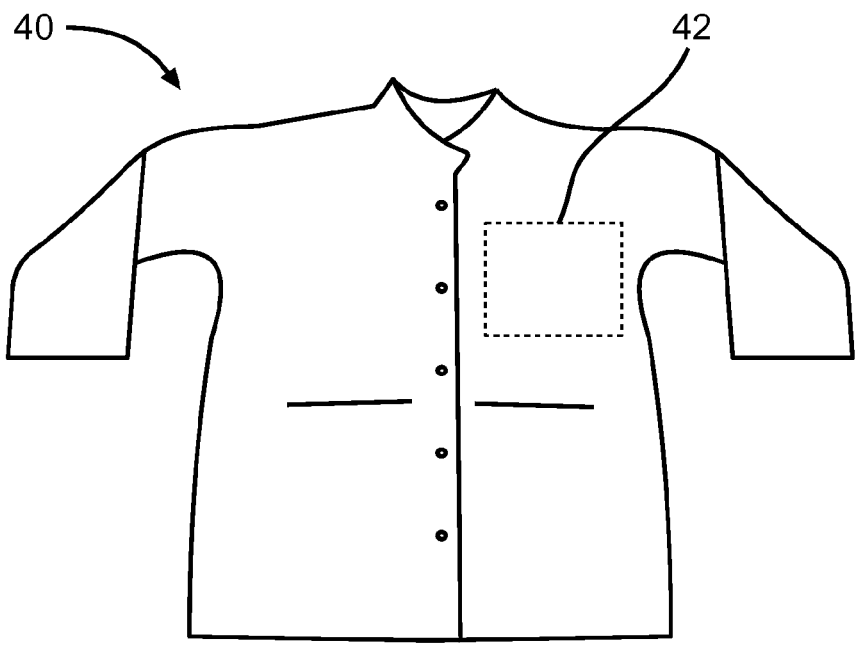
FIGS. 7A-B are perspective views of a welding jacket.
Figure 7B:
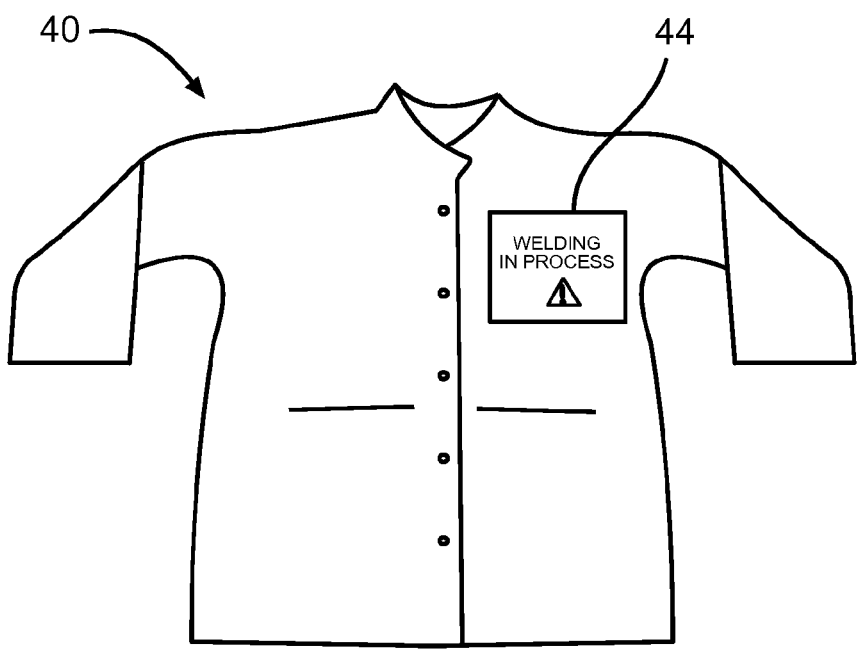

In yet another example, FIGS. 7A and 7B illustrate a welding jacket 40 including a UV exposure indicator 42. The welding jacket 40 may be exposed to an electric welding arc and the UV radiation generated by the electric welding arc. Upon exposure, the indicator may transition from a first image to a second image. As shown in FIG. 7B, the second image may be a message 44 indicating that welding operations are in progress. In such an example, it is contemplated that the primary UV sensitivity would be in the UV-C band such that the message 44 would be activated principally by arc welding, as opposed to natural sunlight. Such an example may be used in a welding environment that is open and exposed to the sun.

Also disclosed is a system for detecting UV radiation exposure during welding operations comprising a welding system adapted to generate an electric welding arc during a welding operation, the electric welding arc generating UV radiation; a welding accessory having a UV exposure indicator; and the UV exposure indicator having at least a first state and a second state, the UV exposure indicator including a UV activated dye adapted to provide a reversible visual indication upon exposure to UV radiation generated by the electric welding arc during the welding operation, the visual indication being a transition from the first state to at least the second state of the UV exposure indicator upon exposure to UV radiation generated by the electric welding arc during the welding operation.

As previously explained, in a welding environment 10, a welding system 14 may generate an electric welding arc between a welding gun 16 or another welding apparatus and a work piece 18, where the electric welding arc generates UV radiation. Referring to FIGS. 2 through 4, a welding accessory, such as welding helmet 12, may have UV exposure indicator. The UV exposure indicator may be a portion of the outer surface 22 of the welding helmet 22. Alternatively, the UV exposure indicator may be a separate component, such as an adhesive backed indicator, that may be attached to the welding accessory.

The UV exposure indicator may have at least a first state and a second state. Referring to FIG. 2, a first state of the UV exposure indicator may be the undecorated outer surface 22 of the welding helmet 12. A second state may be a symbol 26 or logo 28 appearing on the outer surface 22 of the welding helmet 12 after exposure to UV radiation, as shown in FIGS. 3 and 4. Similarly, as shown in FIGS. 5A and 5B, the first state may be a primary image 58 and the second state may be a secondary image 60 displayed along with the primary image 58.

The UV exposure indicator may provide a reversible visual indication upon exposure to UV radiation. For example, the UV exposure indicator portion of welding helmet 12 may transition from the primary image 58 to the secondary image 60 in the presence of UV radiation, and may subsequently transition from secondary image 60 back to primary image 58 when the UV radiation is no longer present. Various UV activated dyes are known that provide a temporary or reversible response to exposure to UV radiation, including UV activated dyes previously discussed. A UV activated dye may be selected to provide a desired degree of persistence for the second state. For example, the second state may be persistent for at least 2, 3, 5, 10, or 15 minutes or any other suitable time period after exposure to UV radiation from the electric welding arc has ceased.

Figure 8A:
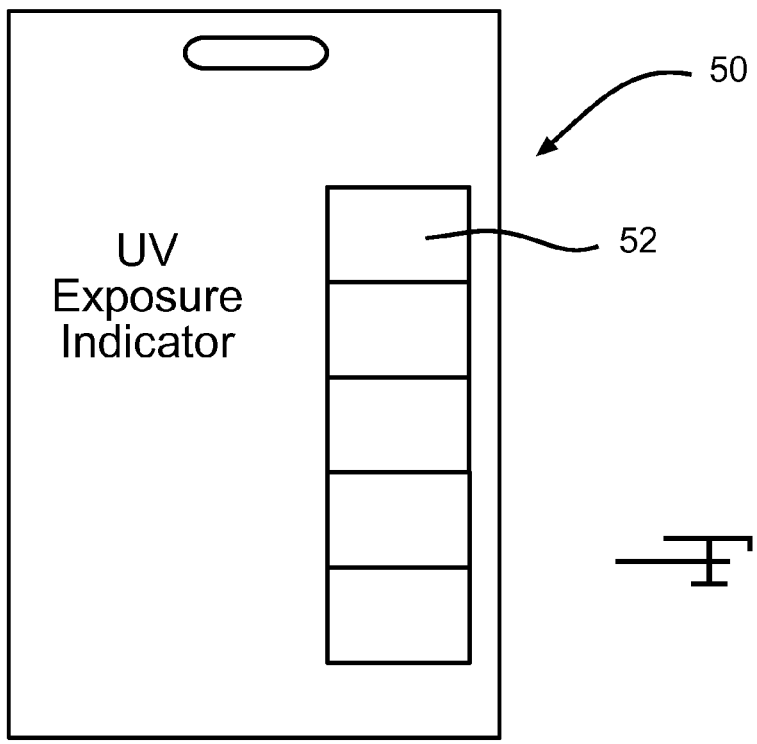
FIGS. 8A-B are perspective views of a UV indicator badge.
Figure 8B:
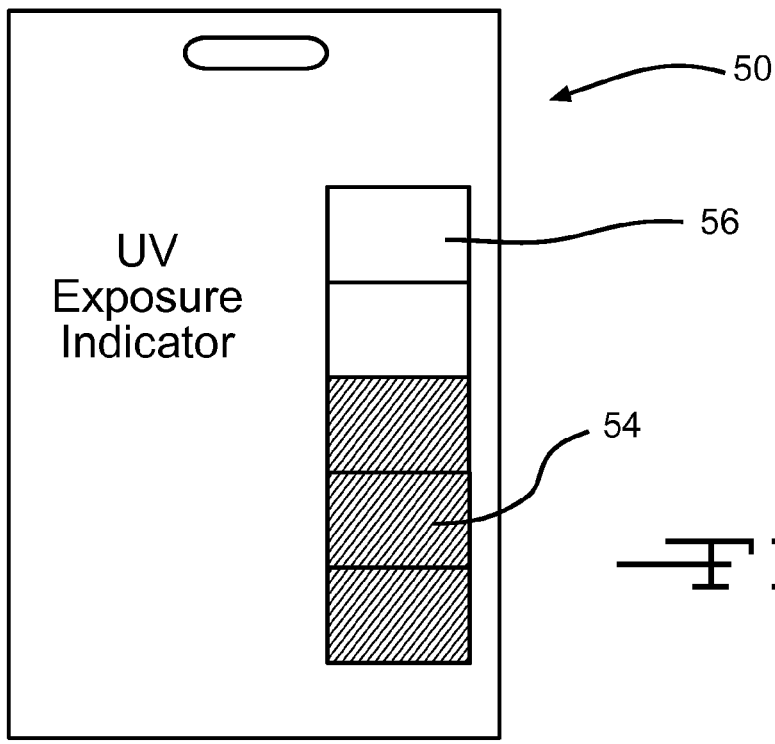

Referring to FIGS. 8A and 8B as an example, a UV exposure indicator may also have multiple states corresponding to the intensity of UV radiation exposure. In one example, the UV exposure indicator may be a badge 50 including a graduated portion 52 serving as a UV exposure indicator and including one or more UV activated dyes. The graduated portion 52 may transition between a first state and a second state upon exposure to a predetermined intensity of UV radiation. The graduated portion 52 may transition to a third state and one or more additional states upon exposure to greater intensities of UV radiation. For example, FIG. 8B illustrates the badge 50 with an activated portion 54 and an unactivated portion 56 of the graduated portion 52. As illustrated, the graduated portion 52 may be divided into discrete sections each corresponding to a predetermined intensity of UV radiation, but discrete portions are not required and a graduated portion 52 with a substantially continuous variation is contemplated.

The transition from the first state to the second state of the UV exposure indicator may comprise a visual indication, such as a change of color in the visual spectrum. The change of color may include changing between different colors or may include changing between different shades of a single color. As previously discussed, the second state may include a logo, symbol, text, or other decorative or informational design. The UV exposure indicator may be incorporated with a welding helmet, where the UV exposure indicator is integrated with the outer surface of the welding helmet. A UV exposure indicator as described herein may also be integrated with the inner surface of a welding helmet to indicate ingress of UV radiation inside the welding helmet during a welding operation. Such ingress of UV radiation may indicate a defect in the welding helmet reducing its effectiveness in protecting the eyes and head of the welder from UV radiation.

Other designs of UV exposure indicators are also possible. For example, a UV exposure indicator including a UV activated dye may be formed on a substrate with an adhesive backing, such as a sticker, and be applied to articles of clothing worn by personnel near a welding operation. Such indicators would provide a convenient means for monitoring UV exposure particularly for visitors or guests unaccustomed to working in a welding environment. The UV exposure indicator may be responsive to UV radiation having a wavelength in the range of 10 to 400 nanometers. Alternatively, the UV exposure indicator may be responsive to UV radiation having a wavelength in the range of 200 to 290 nanometers.

Also disclosed is a system for detecting cumulative UV radiation exposure during welding operations comprising a welding system adapted to generate an electric welding arc during a welding operation, the electric welding arc generating UV radiation; a welding accessory having a UV exposure indicator; and the UV exposure indicator having graduated states, the UV exposure indicator including a UV activated dye adapted to provide a visual indication upon exposure to UV radiation generated by the electric welding arc, the visual indication being a transition between the graduated states to indicate cumulative UV exposure upon exposure to UV radiation generated by the electric welding arc during the welding operation.

As explained above, a badge 50 may have a graduated portion 52 adapted to indicate levels of UV exposure by the transition between graduated states. UV activated dyes are known that provide an irreversible change upon exposure to UV radiation. Such dyes may be referred to as photochangeable or photoreactive and are also commercially available. UV activated dyes as used herein may also refer to these types of dyes.

The graduated portion 52 may be adapted to transition between states to indicate cumulative UV radiation exposure. Each section of the graduated portion 52 may be selected to transition upon a predetermined level of UV radiation exposure. Persons working in or near a welding environment may therefore be able to monitor their cumulative UV radiation exposure and take appropriate preventative or protective measures to safeguard against the effects of such exposure.

Also disclosed is a method for detecting UV radiation exposure during a welding operation comprising providing a welding system adapted to generate an electric welding arc during a welding operation, the electric welding arc capable of generating UV radiation; providing a UV exposure indicator with at least a first state and a second state, the UV exposure indicator including a UV activated dye adapted to provide a visual indication upon exposure to UV radiation generated by the electric welding arc, the visual indication being a transition from the first state to at least the second state of the UV exposure indicator; operating the welding system to generate the electric welding arc generating UV radiation causing the UV exposure indicator to transition between at least the first state and the second state to indicate exposure to UV radiation from the electric welding arc; and monitoring the UV exposure indicator and ceasing the welding operation after a predetermined level of UV exposure is indicated on the UV exposure indicator.

As explained above, a UV exposure indicator may indicate both the presence of UV radiation and may be adapted to indicate the intensity of UV radiation. In some circumstances, it may be desired to cease welding operations when a predetermined level of UV radiation is present as indicated by the UV exposure indicator. Alternatively, additional protective measures, such as curtains or shields, may be required when UV radiation levels in the welding environment exceed predetermined levels. The method for detecting UV radiation exposure during a welding operation may thus provide information to the welding operator and the other persons in the welding environment to ensure that proper safety precautions are followed.

Also disclosed is a method for detecting cumulative UV radiation exposure during a welding operation comprising providing a welding system adapted to generate an electric welding arc during a welding operation, the electric welding arc capable of generating UV radiation; providing a UV exposure indicator with graduated states, the UV exposure indicator including a UV activated dye adapted to provide a visual indication upon exposure to UV radiation generated by the electric welding arc, the visual indication being a transition between the graduated states to indicate cumulative UV exposure; operating the welding system to generate the electric welding arc generating UV radiation causing the UV exposure indicator to transition between the graduated states to indicate exposure to UV radiation from the electric welding arc; and monitoring the UV exposure indicator and ceasing the welding operation after a predetermined level of cumulative UV exposure is indicated on the UV exposure indicator.

While certain embodiments have been described, it must be understood that various changes may be made and equivalents may be substituted without departing from the sprit or scope. In addition, many modifications may be made to adapt a particular situation or material to the teachings of the disclosure without departing from its spirit or scope.

What is claimed is:

1. A welding accessory comprising:
   a surface for exposure to an electric welding arc during a welding operation, the surface having a first image and a second image,
   the first image being visible on the surface of the welding accessory without exposure to the electric welding arc, and
   the second image formed from UV activated dye on the surface and visible only after exposure to UV radiation generated by the electric welding arc during the welding operation and wherein the second image formed from UV activated dye on the surface is reversible to be non-visible after withdrawal from exposure to the UV radiation generated by the electric welding arc during the welding operation.

2. The welding accessory of claim 1, wherein
the welding accessory is selected from the group consisting of welding helmets, welding jackets, hard hats, cloth skull caps, ball cap style hats, welding shirts, safety glasses, gloves, badges, work boots, belts, and jewelry.

3. The welding accessory of claim 1, wherein
the UV activated dye is responsive to UV radiation having a wavelength between 200 and 290 nanometers.

4. The welding accessory of claim 1 where
the second image formed from UV activated dye on the surface is visible only after exposure to a predetermined amount of UV radiation generated by the electric welding arc during the welding operation.

5. A system for detecting UV radiation exposure during welding operations comprising:
   a welding system adapted to generate an electric welding arc during a welding operation, the electric welding arc generating UV radiation;
   a welding accessory having a UV exposure indicator; and
   the UV exposure indicator having at least a first state and a second state, the UV exposure indicator including a UV activated dye adapted to provide a visual indication upon exposure to UV radiation generated by the electric welding arc during the welding operation, the visual indication being a transition from the first state to at least the second state of the UV exposure indicator upon exposure to UV radiation generated by the electric welding arc during the welding operation.

6. The system of claim 5, wherein
the visual indication is a color change in the visual spectrum.

7. The system of claim 5, wherein
the second state comprises a symbol.

8. The welding accessory of claim 5, wherein
the welding accessory is selected from the group consisting of welding helmets, welding jackets, hard hats, cloth skull caps, ball cap style hats, welding shirts, safety glasses, gloves, work boots, belts, and jewelry.

9. The system of claim 5, wherein
the welding accessory is a welding helmet, where the UV exposure indicator is integrated with an outer surface of the welding helmet.

10. The system of claim 5, wherein
the welding apparel is a welding helmet, where the UV exposure indicator is integrated onto the inner surface of the welding helmet to indicate ingress of UV radiation inside the welding helmet during the welding operation.

11. The system of claim 5, wherein
the UV exposure indicator is a sticker adapted to be applied to articles of clothing worn by personal near the welding operation.

12. The system of claim 5, wherein
the UV radiation has a wavelength in the range of 10 to 400 nanometers.

13. The system of claim 5, wherein
the UV radiation has a wavelength in the range of 200 to 290 nanometers.

14. The system of claim 5, wherein
the UV activated dye provides a visual indication upon exposure to a predetermined amount of UV radiation.

15. The system of claim 5, wherein
the visual indication being reversible.

16. The system of claim 15, wherein
the visual indication is persistent for at least about 2 minutes after exposure to UV radiation.

17. The system of claim 5, wherein
the UV exposure indicator has graduated states, where the visual indication is a transition between the graduated states to indicate cumulative UV exposure upon exposure to UV radiation generated by the electric welding arc during the welding operation.

18. A method for detecting UV radiation exposure during a welding operation comprising:
   providing a welding system adapted to generate an electric welding arc during a welding operation, the electric welding arc capable of generating UV radiation;
   providing a UV exposure indicator with at least a first state and a second state, the UV exposure indicator including a UV activated dye adapted to provide a visual indication upon exposure to UV radiation generated by the electric welding arc, the visual indication being a transition from the first state to at least the second state of the UV exposure indicator;
   operating the welding system to generate the electric welding arc generating UV radiation causing the UV exposure indicator to transition between at least the first state and the second state to indicate exposure to UV radiation from the electric welding arc; and monitoring the UV exposure indicator and ceasing the welding operation after a predetermined level of UV exposure is indicated on the UV exposure indicator.

19. A system for detecting UV radiation exposure during welding operations comprising:

a welding system adapted to generate an electric welding arc during a welding operation, the electric welding arc generating UV radiation;

a welding accessory having a means for indicating UV exposure; and the means for indicating UV exposure having at least a first state and a second state and including a means for providing a visual indication upon exposure to UV radiation generated by the electric welding arc during the welding operation.

* * * * *

UNITED STATES PATENT AND TRADEMARK OFFICE
CERTIFICATE OF CORRECTION

PATENT NO. : 8,284,385 B2  
APPLICATION NO. : 12/618231  
DATED : October 9, 2012  
INVENTOR(S) : Bruce John Chantry et al.

Page 1 of 1

It is certified that error appears in the above-identified patent and that said Letters Patent is hereby corrected as shown below:

Column 4, Line 67, please delete

"{N-[[4-(dimethylamino)phenyl] phenylmethylene-2.5-cyclohexyldien-1-ylidene]-N-methyl-methanaminium chloride or bis[p-(dimethylamino)phenyl]phenylmethylium chloride},"

and insert

--"{N-4-[[4-(dimethylamino)phenyl]phenylmethylene-2.5-cyclohexyldien-1-ylidene]-N-methyl-methanaminium chloride or bis[p-(dimethylamino)phenyl]phenylmethylium chloride}--.

Signed and Sealed this  
Twelfth Day of February, 2013

Teresa Stanek Rea  
*Acting Director of the United States Patent and Trademark Office*